(12) United States Patent
McInroy et al.

(10) Patent No.: US 9,849,182 B2
(45) Date of Patent: Dec. 26, 2017

(54) WOUND TREATMENT

(75) Inventors: Lorna McInroy, Earby (GB); Rachael Louise Clark, Skipton (GB); Michelle Delbono, Barnoldswick (GB); Lorraine Nisbet, Skipton (GB); Paul Howard Lowing, Keighley (GB)

(73) Assignee: KCI USA, Inc., San Antonio, TX (US)

( * ) Notice: Subject to any disclaimer, the term of this patent is extended or adjusted under 35 U.S.C. 154(b) by 0 days.

(21) Appl. No.: 14/115,065

(22) PCT Filed: Apr. 24, 2012

(86) PCT No.: PCT/GB2012/000379
§ 371 (c)(1),
(2), (4) Date: Apr. 21, 2014

(87) PCT Pub. No.: WO2012/150429
PCT Pub. Date: Nov. 8, 2012

(65) Prior Publication Data
US 2014/0241997 A1    Aug. 28, 2014

(30) Foreign Application Priority Data

May 3, 2011 (GB) .................... 1107378.0

(51) Int. Cl.
*A61K 47/36* (2006.01)
*A61L 26/00* (2006.01)

(52) U.S. Cl.
CPC ............ *A61K 47/36* (2013.01); *A61L 26/008* (2013.01); *A61L 26/0023* (2013.01); *A61L 26/0066* (2013.01)

(58) Field of Classification Search
CPC ...................................................... A61K 47/36
See application file for complete search history.

(56) References Cited

U.S. PATENT DOCUMENTS

| | | | |
|---|---|---|---|
| 5,804,213 A | 9/1998 | Rolf | |
| 6,174,544 B1 | 1/2001 | Jensen | |
| 2005/0129744 A1* | 6/2005 | Caldwell | A61F 17/00 424/443 |
| 2007/0020318 A1* | 1/2007 | Silcock | A61L 15/28 424/445 |
| 2007/0218285 A1 | 9/2007 | Malessa | |

FOREIGN PATENT DOCUMENTS

| | | | |
|---|---|---|---|
| DE | 102006029500 A1 | 1/2008 | |
| EP | 0380253 A2 | 8/1990 | |
| EP | 0567311 A2 | 4/1993 | |
| EP | 1666020 A1 | 6/2006 | |
| GB | 1122796 A | 8/1968 | |
| NL | EP 1243246 A1 * | 9/2002 | ............... A61K 6/10 |
| WO | 97/33632 | 9/1997 | |
| WO | 2004/080343 A2 | 9/2004 | |
| WO | 2005/023176 A2 | 3/2005 | |
| WO | 2006/065349 A2 | 6/2006 | |
| WO | 2007/048193 A1 | 5/2007 | |
| WO | 2008/072117 A2 | 6/2008 | |
| WO | 2010/070292 A1 | 6/2010 | |
| WO | 2012/150429 A1 | 11/2012 | |

OTHER PUBLICATIONS

UKIPO Search Report dated Aug. 18, 2011 2 pages.
UKIPO Search Report dated Sep. 20, 2011 2 pages.
Tachi et al: "Comparison of bacteria-retaining ability of absorbent wound dressings" © Blackwell Publishing Ltd and Medicalhelpliness.com Inc. 2004 • International Wound Journal • vol. 1 No. 3 pp. 177-181.
Newman et al: "Visualisation of bacterial sequestration and bactericidal activity within hydrating Hydrofiber® wound dressings"—Biomaterials 27 (2006) pp. 1129-1139.
PCT International Search Report in corresponding International Application No. PCT/GB2012/000379 dated Jun. 14, 2012 (4 pages).

* cited by examiner

*Primary Examiner* — Jessica Worsham

(57) ABSTRACT

Use of a moulding composition comprising a polymer and a setting agent for wound debridement, wherein said use comprises adding water to said moulding composition to form a moulding fluid, applying said moulding fluid to a surface of a wound, allowing said moulding fluid to set in contact with said surface to form a solid covering on said surface, followed by removing said solid covering from the wound. The alginate composition adheres strongly to bacterial biofilms on the wound, whereby the biofilms are removed with the alginate composition. The moulding composition may be used in conjunction with a staining agent that undergoes a color change in the presence of bacteria or bacterial polysaccharides to show the presence and removal of the biofilm. Also provided are methods of treating wounds using the compositions.

29 Claims, No Drawings

WOUND TREATMENT

The present invention relates to wound treatment, in particular the detection and removal of biofilm, and wound debridement.

When the skin is broken and a wound is produced, the normal wound healing process begins. In healthy individuals there are essentially three phases of wound healing—the inflammatory phase, proliferation phase and the remodelling phase. The inflammatory phase begins at the time of injury and usually lasts for four to six days. The wound is cleansed of bacteria and debris, and is prepared for healing. During the proliferation stage the wound contracts and granulation tissue is formed to fill in the defect. In an acute wound with no factors to impair the healing, two to three weeks is all that is necessary to close even large wounds. In the final remodelling phase, the wound healing process continues, and the tissue ideally returns to its original strength. This phase may last from twenty one days to two years.

Wound healing becomes less straightforward in individuals who have associated medical problems. In some cases wounds cease to heal and become "chronic wounds" which remain in the inflammatory stage.

Wound bacterial biofilms can contribute to the development of non-healing wounds. It is well known that bacteria naturally form biofilms when they are able to associate with an open wound. Non-healing wounds are often associated with individuals with impaired inflammatory response, so bacteria can persist within a wound and establish a biofilm community with cannot be overcome by the individual's natural defences alone.

Biofilm removal from wounds is usually carried out via debridement. Debridement is the removal of necrotic, damaged or infected tissue from and around a wound to expose healthy tissue. There are number of debridement techniques, the quickest and most selective of which is surgical debridement, in which a scalpel, scissors, or other instrument (including a laser) is used to cut necrotic tissue from a wound. However, during surgical debridement, underlying tendons, blood vessels and other structures may be damaged. Surface bacteria may also be introduced deeper into the body. Less invasive debridement methods may be used; for example mechanical debridement, in which a saline-moistened dressing is allowed to dry and adhere to the dead tissue. When the dressing is removed, the dead tissue is also removed. However, the method is non-selective and may traumatise healthy or healing tissue, causing the patient severe pain.

Anti-biofilm agents may also be used to reduce the presence of biofilm. Anti-biofilm agents have been used in a number of industries such as water treatment, food processing, beef processing, dairy and dentistry. One such agent is bovine lactoferrin. *Pseudomonas* in the presence of bovine lactoferrin will divide normally but is unable to attach, and therefore unable to form biofilm structures. Bovine lactoferrin is used in the beef industry on the carcasses of meat to prevent biofilm formation.

An associated problem is the detection of biofilm at first instance. Even if there is no evidence of clinical infection, it is likely that biofilm bacteria play a large role in preventing the normal healing process from occurring. The nature of biofilm means that, unlike planktonic bacteria, it has a number of pathways to down-regulate its virulence, so that does not significantly damage the host. Due to this modulation of risk factors, clinical signs of infection are often not obvious.

Accordingly, it is an object of the present invention to provide an improved method of treatment of wounds. In particular, the present invention is directed to improved compositions, kits and methods for treatment of bacterial biofilms in wounds. The present invention is also directed to improved compositions, kits and methods for debridement of wounds.

Alginate impression materials have been used for many years in dentistry to make impressions for prosthodontic, orthodontic or other appliances. Alginate casting materials are also widely used for craft and hobby preparation of moulding casts. The present inventors have found that, surprisingly, alginate-containing compositions have a high affinity for biofilm and necrotic tissue. Accordingly, alginate-containing compositions may be of use in the treatment of wounds, in particular for wound debridement and biofilm removal.

The use of alginates, in particular alginate fibers, fabrics and hydrogels, as wound dressing materials is known. The alginate provides a wound-friendly, hydrophilic, non-adherent and bioabsorbable wound contacting surface to the dressing. The alginate dressings are left in contact with the wound for extended periods of at least several hours to promote wound healing. They are designed to be non-adherent to reduce wound trauma when the dressing is removed. In particular, they form an alginate hydrogel with wound fluid. The hydrogel has low physical strength and is non-adherent to the wound surface.

DE-A-102006029500 describes alginate compositions that harden to a dimensionally stable alginate mass for application to wounds. The compositions contain an antimicrobial agent, and also contain a water-absorbing component such as a hydrocolloid to produce an absorbent wound dressing composition in situ on a wound.

WO-A-2007048193 describes wound dressing compositions that are solid, particulate mixtures of alginates in a low-water-activity antimicrobial matrix such as honey.

WO-A-2005023176 describes hydrogel compositions for the delivery and sustained release of active agents to a wound. The hydrogel is formed in situ on the wound by gelling of an anionic polysaccharide with calcium ions present in biological fluids. GB-A-1122796 and WO-A-2004080343 describe applying an alginate hydrogel dressing onto wounds by sequentially applying a sodium alginate solution and a calcium chloride solution to the wound.

EP-A-1666020 describes fluid alginate compositions containing a gelling agent that can be applied to a wound. The compositions set to form a hydrogel wound dressing in contact with the wound. The compositions further contain foaming agents to generate carbon dioxide. EP-A-0380253 describes another alginate composition that forms a foamed hydrogel following application to a wound.

WO-A-9733632 describes fluid gel compositions that can be applied to wounds containing a slow release gelling agent and an antimicrobial agent.

U.S. Pat. No. 6,174,544 describes the use of an alginate gel for wound filling, in combination with a dressing containing calcium salts that leach into the gel to harden the gel so that the gel can be removed easily.

US-A-2007218285 describes alginate casting compositions for forming porous moulded articles. The moulded articles may be used for cosmetic purposes, such as skin pads and face packs. The porous moulded articles may be used as wound dressings.

Newman et al. in *Biomaterials, vol. 27(7)*, pages 1129-1139 (2006) describes treating sodium carboxymethylcellulose hydrogel-forming fiber dressings with fluorescent dyes to visualise bacterial activity.

WO-A-2008072117 describes incorporating dyes into cyanoacrylate skin sealants. The dyes change colour in the presence of microorganisms to provide an indication of infection.

WO-A-2010070292 describes compositions for application to skin or wounds, wherein the compositions contain colorants that are capable of preferentially staining biofilms.

WO-A-2006065349 describes elastomeric articles, such as surgical gloves, that contain a dye that changes colour in the presence of microorganisms.

In a first aspect, the present invention provides the use of a moulding composition comprising a polymer and a setting agent for wound debridement, wherein said use comprises adding water to said moulding composition to form a moulding fluid, applying said moulding fluid to a surface of a wound, allowing said moulding fluid to set in contact with said surface to form a solid covering on said surface, followed by removing the solid covering from the wound.

Certain polymers and salts thereof are water soluble, but when combined with a setting agent and water, form a moulding fluid, which will set in time, to form a moulded solid on the surface with which it is in contact. In accordance with the present invention, the moulding fluid is allowed to set in contact with the surface of a wound. The set moulding composition adheres only weakly to the skin and wound surface. When the solidified moulding material is then removed from the wound, biofilm is also removed. The term "wound debridement" herein refers to such removal of bacterial biofilms from the wound. Necrotic tissue, when present, is also removed from the wound.

Suitably, the polymer and the setting agent are in the form of particulate solids, such as powders. The powders may be provided separately or in admixture prior to use. In any event, water is added to the components with mixing to form a moulding fluid. Suitably, the moulding composition and water are vigorously mixed until a pourable or spreadable consistency is reached.

Once the moulding fluid has set, the resulting moulded solid may be left on the surface of the wound for a period of time. Alternatively, once the moulding fluid has set in contact with the surface of the wound, it may then be removed immediately from the surface of the wound. Suitably, the setting time of the moulding fluid is sufficient that the moulding composition may be applied to the wound surface, without undue haste. Suitably, the moulded solid is removed from the wound from about 2 minutes to about 6 hours after application, typically from about 5 minutes to about 1 hour after application, for example within 30 minutes of application.

More than one application and subsequent removal of the moulding fluid may be carried out, depending on the bacterial biofilm population.

Suitably, the polymer comprises or consists essentially of one or more polysaccharides. The polysaccharide may suitably be a polyanionic polysaccharide. Suitably, the anionic polysaccharide is a polycarboxylate. Suitable polysaccharides include alginates, agar, guar gum, hyaluronates, pectins, carrageenans, xanthan gums, sulfate dextrans, cellulose derivatives such as carboxymethyl celluloses, and oxidized celluloses. Especially suitable anionic polysaccharides are water soluble alginates such as sodium alginate. It is thought that the polysaccharide moulding materials have high affinity for glycopolysaccharides and mucopolysaccharides of the biofilm, and that this accounts for the good adhesion of biofilms to the polysaccharide polymers.

Water soluble alginate salts include sodium alginate, potassium alginate, and ammonium alginate. Most suitably, the alginate comprises or consists essentially of sodium alginate.

The polymer may initially be thy mixed with a suitable setting agent to form a composition such that, when the composition is mixed with water, a fluid (pourable or spreadable) moulding composition is obtained. Suitably, the moulding fluid is a spreadable, viscous or thixotropic material, for example it may have a viscosity of from about 1 Pa s to about 300 Pa s, for example from about 10 Pa s to about 100 Pa s. It is therefore considerably more fluid than, for example, alginate dental impression materials. Suitably, the amount of water added to the moulding composition to form the moulding fluid is in a solids:water ratio by weight of about 1:1 to about 3:1. The water content of the moulding composition after it has solidified is therefore suitably from about 25 wt. % to about 50 wt. %. The moulding composition does not absorb significant amount of water in contact with wound fluid, and is non-porous. It therefore differs from the hydrogel-forming alginate wound dressings known in the art, which have high equilibrium water contents and low tensile strength. Suitably, the set moulding composition has an equilibrium water content less than about 50%.

The setting agent for polyanionic polymers may be a divalent (or higher) metal salt. Suitably, the setting agent is a divalent metal salt. Preferably, the setting agent is a calcium salt, suitably a sparingly soluble calcium salt such as calcium sulphate or calcium silicate. Additional salts may be present, in particular antimicrobial salts such as silver salts or zinc salts, or adjusting salts such as phosphates, silicates or carbonates of sodium, calcium or the like. The compositions may comprise a retarder such as trisodium phosphate, which reacts primarily with the calcium salt to retard release of the calcium.

In other embodiments, the polymer may be a guar gum and the setting agent may be a borate salt, such as sodium tetraborate. In yet other embodiments, the polymer may be a water soluble xanthan gum and the setting agent may be a water soluble galactomannan gum, as described in EP-A-0792653.

Suitably, the moulding compositions of the present invention comprise from about 10 wt. % to about 40 wt. % of the polymer, for example from about 12 wt. % to about 30 wt. % of the polymer. Suitably, the moulding compositions of the present invention comprise from about 10 wt. % to about 50 wt. % of the setting agent, for example from about 12 wt. % to about 40 wt. % of the setting agent. All of these percentages are dry weight basis of the moulding composition.

Setting of the polymer suitably results in a coherent solid, plastic, elastic or gel-like mass. The mass suitably has sufficient tensile strength be lifted from the wound in one piece. For example, the set composition may have a tensile strength of at least about 0.1 MPa, suitably at least about 0.3 MPa, more suitably at least about 0.5 MPa. The tensile strength is measured by casting a sheet of the composition approximately 2 mm thick in a flat mould, cutting a strip of dimensions 5 cm×1 cm from the sheet, and measuring the tensile strength of the strip in an Instron or similar apparatus. These tensile strengths are considerably higher than the tensile strength of the alginate hydrogels that have previously been used for wound treatment.

The moulding composition may be chromatic moulding composition, which will undergo a colour change when mixed with water to form a moulding fluid and/or said composition is set (i.e. it is no longer a pourable or spreadable fluid). Suitable indicators include thymolphthalein and phenolphthalein, or mixtures thereof. These indicators turn a sodium alginate/calcium sulphate moulding composition from white to pink when water is added to form the moulding fluid, then back to white when the composition has set.

It is envisaged that the moulding composition could be mixed with water to form a moulding fluid. This mixing could be carried out in the vicinity of the patient, as no specialist equipment is required. The moulding fluid could then be spread onto/poured onto and around the wound area and allowed to set (i.e. until the composition is no longer fluid). Advantageously, the moulding composition can cover an area of any required size. Conventional wound dressings are manufactured in various different sizes, and the most appropriate size must be selected. Using the moulding fluid of the present invention, a wound treatment of potentially any size or shape is provided.

Furthermore, conventional wound dressings may not make contact with the wound surface without the application of pressure, potentially causing the patient discomfort. The nature of the moulding fluid used in the present invention allows an exact impression of the wound surface to be made in effect providing a custom made wound treatment.

Wounds located on joints or protrusions (such as the ankle) may be difficult to treat using conventional wound dressings, due to their non-uniform shape. The moulding fluid used in the present invention may be easily poured onto the area, before being allowed to set. Suitably, the moulding composition used in the present invention is sterile. This could be achieved by autoclaving, treatment with ethylene oxide, dry heat sterilisation or gamma irradiation. The sterilization would suitably be performed on the dry polymer and setting agent, for example packaged, either separately in admixture. Addition of sterile water would then result in a sterile moulding composition for application to the wound.

The moulding composition of the present invention may comprise further elements. The moulding composition may comprise a filler. Suitable fillers include diatomaceous earth, anhydrous silicate, talc, calcium carbonate, pearlite, silica, cellulose and aluminium hydroxide. The filler is suitably admixed with the polymer and optionally also with the setting agent prior to use. For example, the invention contemplates dry mixtures of filler, polymer and setting agent, preferably sterile and packaged. Suitably, the moulding compositions of the present invention comprise from about 10 wt. % to about 80 wt. % of one or more inert fillers, for example from about 40 wt. % to about 70 wt. % of one or more inert fillers on dry weight basis.

The compositions used in the invention may further comprise one or more plasticisers. The optional plasticisers assist in providing a flexible, soft cured material in situ in the wound. Suitable plasticisers include medically acceptable mineral oils, silicone oils, vegetable oils, stearates, hydrogenated ethers and esters, and mixtures thereof. The plasticisers may be present, for example, in an amount of from about 1 wt. % to about 20 wt. % of the composition on dry weight basis.

The compositions used in the invention may further comprise one or more humectants. The optional humectants assist in maintaining the desired hydrophilic property of the composition. Suitable humectants include medically acceptable polyhydric alcohols such as glycerol, sorbitol, soft paraffin, urea 25 creams, lanoline, sodium pyrrolidone carboxylate (PCANa), gamma linolenic acid (evening primrose oil) and soya oil, tea tree oil, coconut oil (or any other nut oil), camomile, aloe vera, jojoba oil, cocoamide or mixtures thereof. The humectants may be present, for example, in an amount of from about 0.1 wt. % to about 10 wt. % of the composition on dry weight basis.

The moulding composition of the present invention may further comprise an active pharmaceutical ingredient, such as a topical antimicrobial agent. Suitable topical antimicrobials include antibiotics such as Bacitracin or Neosporin, chlorhexidine, Laurie arginate, metallic silver, and silver compounds such as Silver sulfadiazine. Suitably, the active pharmaceutical ingredient is present in an amount of from about 0.001 wt. % to 5 wt. %, for example from about 0.1 wt. % to about 2 wt. % based on the dry weight of the composition.

In embodiments, the method further comprises applying to the wound a staining agent that undergoes a colour change in the presence of bacteria or bacterial polysaccharides.

The water soluble polymer and the setting agent may be dry packaged together before use, for example as a kit with the staining agent packaged separately from the water soluble polymer and the setting agent.

The staining agent will undergo a colour change in the presence of bacteria or bacterial polysaccharide. Staining agents of this type are described in WO-A-2010070292, WO-A-2006065349 and WO-A-2008072117. A suitable staining agent is a copper phthalocyanine dye. An example of a copper phthalocyanine dye is Alcian blue, which is also known as Alcian blue SGX, Ingrain blue 1, and C.I. 74240. Alcian blue specifically binds to polysaccharides, staining them blue-green. As biofilm contains polysaccharide, Alcian blue can be used as stain to indicate the presence of biofilm on a wound surface.

The use of a staining agent to indicate areas of significant biofilm will allow areas of high bacterial burden to be directly treated by debridement. This visual indication of biofilm burden will prevent over-debridement and incorrect diagnosis. The removal of the coloured staining agent onto the solidified alginate composition also gives visual proof of the effectiveness of the debridement.

In a further aspect, the present invention provides a method of treating a wound comprising the steps of mixing a moulding composition comprising a polymer and a setting agent for said polymer with water to form a moulding fluid; applying said moulding fluid to a surface of a wound, allowing said moulding fluid to set in contact with said surface, followed by removing said moulding composition from the wound. Suitably, the moulding composition is as described above in relation to the first aspect of the invention. Suitably, the method further comprises applying a staining as described above to the wound prior to the application of the moulding fluid.

In embodiments, the wound may be a chronic wound such as a dermal ulcer. The uses and methods according to the present invention suitably do not comprise application the composition to mucous membranes, teeth, or gums.

It will be appreciated that any feature or embodiment disclosed herein in relation to any one embodiment of the invention may also be applicable to any of the other embodiments. This applies in particular to the components and composition of the moulding composition.

All patent publications referred to herein are hereby expressly incorporated in their entirety.

EXAMPLE 1—USE OF ALCIAN BLUE AS A BIOFILM STAINING AGENT

Pieces of raw chicken breast meat were studied as a model for biofilm and necrotic tissue formation. The first three pieces were inoculated with *Pseudomonas aeruginosa* before being left at 37° C. for 24-48 hr. A solution of Alcian blue was then applied to the surface of the chicken. Areas of blue-green staining indicated the presence of bacterial biofilm. As expected, the chicken pieces that were inoculated had a higher bacterial biofilm population than non-inoculated pieces containing the normal flora.

EXAMPLE 2—FORMATION AND APPLICATION OF THE MOULDING FLUID

Life Casting Alginate (obtained from Craftwise Ltd) was mixed vigorously with an equal volume of cold water. Once a porridge-like consistency was obtained, the moulding fluid was applied to pieces of chicken, prepared according to Example 1. The composition was left for about 30 minutes to set completely, after which the resulting flexible mould material was separated from the chicken pieces. It was observed that the removal of the composition from the chicken pieces also removed large amounts of biofilm, as indicated by the blue-green staining on the inner surface of the removed moulding material. The procedure was repeated for a piece of chicken which was subjected to two consecutive applications (followed by removals) of the fluid forming composition. It was evident that the second cast also removed necrotic material, indicated by the presence of the blue-green stain on the inside of the cast and of the necrotic, yellow tissue itself.

The invention claimed is:

1. A method for treating a wound, comprising:
   adding water to a moulding composition comprising a polymer and a setting agent to form a moulding fluid, wherein the polymer comprises at least one polysaccharide, and the setting agent comprises a divalent metal salt; wherein the polymer and the setting agent are solids, and the moulding fluid comprises a solids to water ratio by weight of between 1:1 and 3:1; applying said moulding fluid to a surface of said wound, allowing said moulding fluid to set in contact with said surface to form a solid covering; and
   removing said solid covering from said wound to debride said wound; wherein the removing is performed not more than six hours after the applying.

2. A method according to claim 1, wherein said polysaccharide is a polyanionic polysaccharide.

3. A method according to claim 2, wherein said polyanionic polysaccharide is sodium alginate and said setting agent comprises calcium sulphate.

4. A method according to claim 1, wherein said moulding composition further comprises a filler in an amount of from about 10% to about 70% dry weight basis.

5. A method according to claim 1, wherein said polymer and said setting agent are in the form of particulate solids in admixture.

6. A method according to claim 1 wherein said moulding composition comprises from about 12% to about 30% dry weight basis of the polymer and from about 12% to about 40% dry weight basis of the setting agent.

7. A method according to claim 1, wherein said moulding composition further comprises an antimicrobial agent.

8. A method according to claim 1, wherein said method further comprises applying to said wound a staining agent, wherein said staining agent is adapted to undergo a colour change in the presence of bacteria or bacterial polysaccharides.

9. A method according to claim 8, wherein the staining agent is a copper phthalocyanine dye.

10. A method according to claim 1, wherein said step of removing is performed not more than about one hour after said step of applying.

11. A method according to claim 1, wherein said step of removing is performed not more than about 30 minutes after said step of applying.

12. A method according to claim 1, wherein said moulding fluid is a chromatic composition that undergoes a colour change when it sets.

13. A method according to claim 1, wherein said setting agent comprises a calcium salt.

14. A method according to claim 13, wherein said calcium salt is calcium sulphate or calcium silicate.

15. A method according to claim 13, wherein said setting agent further comprises a silver salt or zinc salt.

16. A method according to claim 13, wherein said moulding composition further comprises a retarder adapted to react with said calcium salt to retard the release of calcium.

17. A method according to claim 16, wherein said retarder is trisodium phosphate.

18. A method according to claim 1, wherein said moulding composition further comprises one or more plasticisers.

19. A method according to claim 1, wherein said moulding composition further comprises one or more humectants.

20. A method according to claim 1, wherein said solid covering has a water content from about 25 wt. % to about 50 wt. %.

21. A method according to claim 8, wherein said method further comprises applying to said wound the staining agent prior to applying said moulding fluid.

22. A method for debriding a wound, comprising:
   applying an aqueous moulding fluid to a surface of said wound, said aqueous moulding fluid comprising (a) a polymer selected from the group consisting of sodium alginate, guar gum, and xanthan gum, (b) a setting agent selected from the group consisting of a calcium salt, a borate salt, and a water soluble galactomannan gum, and (c) a chromatic indicating agent that undergoes a colour change; and (c) a chromatic indicating agent that undergoes a colour change; wherein the polymer and the setting agent are solids, and the moulding fluid comprises a solids to water ratio by weight of between 1:1 and 3:1;
   allowing said aqueous moulding fluid to set in contact with said surface to form a solid covering; and
   removing said solid covering from said wound to debride said wound, wherein the removing is performed not more than six hours after the applying.

23. A method according to claim 22, wherein said polymer is sodium alginate and said setting agent comprises calcium sulphate.

24. A method according to claim 22, wherein said step of removing is performed not more than about one hour after the applying of the moulding fluid.

25. A method according to claim 24, wherein said step of removing is performed not more than about 30 minutes after the applying of the moulding fluid.

26. A method according to claim 22, wherein said solid covering has a water content from about 25 wt. % to about 50 wt. %.

27. A method according to claim 22, wherein said method further comprises applying to said wound a staining agent, wherein said staining agent is adapted to undergo a colour change in the presence of bacteria or bacterial polysaccharides.

28. A method according to claim 22, wherein said aqueous moulding fluid further comprises an antimicrobial agent.

29. A method according to claim 22, wherein said chromatic indicating agent is selected from the group consisting of thymolphthalein, phenolphthalein, and mixtures thereof.

\* \* \* \* \*